United States Patent [19]  [11] 4,002,734
Pickford  [45] Jan. 11, 1977

[54] EMOLLIENT HAIR GROOMING COMPOSITION

[76] Inventor: Melcina H. Pickford, 614 W. Broadway, Minneapolis, Minn. 55411

[22] Filed: Aug. 7, 1975

[21] Appl. No.: 602,663

Related U.S. Application Data

[63] Continuation-in-part of Ser. No. 410,631, Oct. 29, 1973, abandoned.

[52] U.S. Cl. .................... 424/74; 424/DIG. 4; 424/70; 424/165; 424/196
[51] Int. Cl.² .................................. A61K 7/06
[58] Field of Search ........... 424/70, 74 DIG. 4, 196, 424/165

[56] References Cited

UNITED STATES PATENTS

| | | | |
|---|---|---|---|
| 879,191 | 2/1908 | Pieper | 424/74 |
| 1,037,425 | 9/1912 | Brooks | 424/74 |
| 1,365,981 | 1/1921 | Gough | 424/74 |
| 1,525,299 | 2/1925 | Heitkamp | 424/74 |
| 1,600,340 | 9/1926 | Kobbe | 424/70 X |
| 1,852,231 | 4/1932 | Bryner | 424/74 |
| 2,622,596 | 12/1952 | Freed | 424/70 X |
| 2,678,901 | 5/1954 | Fox et al. | 424/70 |
| 2,771,394 | 11/1956 | Mehaffey | 424/74 |
| 2,886,488 | 5/1959 | Berg | 424/70 X |
| 2,942,008 | 6/1960 | Lubowe | 424/70 X |

*Primary Examiner*—Albert T. Meyers
*Attorney, Agent, or Firm*—Burd, Braddock & Bartz

[57] ABSTRACT

A composition for grooming or dressing hair which comprises a blended mixture of minor amounts of petroleum, rectified tar oil, sulfur, phenol, oxyquinoline, pine oil and castor oil in a petroleum jelly base. The material has been found to be useful and effective in grooming the hair, making unruly hair more easily manageable, controlling loose dandruff and lubricating the hair to improve its appearance and texture.

4 Claims, No Drawings

HAIR GROOMING COMPOSITION

This application is a continuation-in-part of application Ser. No. 410,631, filed Oct. 29, 1973; now abandoned.

This invention is directed to an emollient composition for grooming or dressing hair, treating dry scalp and controlling loose dandruff, managing unruly hair, and the like. It is a soothing emollient petroleum jelly base composition of ointment or salve-like consistency easily applied by rubbing into the hair and scalp to control the hair upon combing, to alleviate dry scalp, to control loose dandruff, to alleviate hair damage through mistreatment or abuse, to control unruly or unmanageable hair, or the like.

The emollient composition according to the present invention comprises a blended mixture of minor amounts of petroleum, rectified tar oil, sulfur, phenol, oxyquinoline, pine oil and castor oil in a predominant petroleum jelly base. The composition also desirably contains minor amounts of lanolin and a bacteriacide and fungicide such as captan (N-trichloromethyl-thio-4-cyclohexene-1,2-dicarboximide). Small amounts of mineral oil and waxy materials such as mineral wax, isopropyl palmitate and natural or synthetic beeswax are also desirably included. To alleviate the normal strong odor of the product, an odorant such as rose geranium oil is included.

One convenient means of compounding the emollient material is to blend together the ingredients in the proportion of about 16 to 20 parts by weight of Glover's Sarcoptic Mange Medicine for hair and scalp (a proprietary product of H. Clay Glover Co., Inc., Toms River, New Jersey), which in turn is comprised of rectified tar oil, sulfur, lanolin and captan in a predominant amount of petroleum base, or equivalent mixture, as a first ingredient; about 15 to 19 parts by weight of Cuticura Ointment (manufactured by Purex Corporation, Ltd., of Batavia, Illinois) and comprised of minor amounts of mineral oil, mineral wax, isopropyl palmitate, synthetic beeswax, precipitated sulfur, U.S.P., rose geranium oil, U.S.P., oxyquinoline and pine oil in a predominant carbolated petrolatum (petroleum jelly) base, the mixture containing about 0.1% by weight of phenol, or equivalent mixture, as a second ingredient; and about 14 to 18 parts by weight of castor oil, as a third ingredient; all blended into about 240 to 400 parts by weight of petroleum jelly, as the fourth ingredient.

The blended mixture is prepared by first placing the petroleum jelly into a suitable heatable container distributed as uniformly as possible taking into account the semi-solid consistency of petroleum jelly at room temperature. The Cuticura Ointment or equivalent mixture, the mange medicine or equivalent mixture, and the castor oil are then distributed as uniformly as possible, preferably in that order, over the surface of the petroleum jelly. The mixture is heated slowly to slightly above the melting point of the petroleum jelly (38°–54° C). As the semi-solid ingredients melt, the mixture is stirred constantly until a uniform homogeneous blend of the ingredients is obtained. The blend is then poured into suitable containers, jars, or tubes, and allowed to set up by slowly cooling. The resulting emollient composition is of ointment-like or salve-like consistency. It is easily applied to the hair and scalp by applying a small amount to the finger tips and rubbing.

Glover's Mange Medicine has been used for almost 100 years in the treatment of infectious dandruff and dandruff itch and to obtain relief from dry scalp. When used as directed to lubricate and condition the scalp, the scalp is first massaged, the mange medicine is rubbed in well with the finger tips and left for from 15 minutes to 2 hours and then removed by shampooing the hair and scalp. In contrast, the composition according to the present invention is rubbed in well with the finger tips and left on the hair and scalp. One reason this may be done is that the addition of Cuticura Ointment or equivalent not only aids in promoting healing but eliminates the strong odor of the mange medicine, which many find to be objectionable. The petroleum jelly, in addition to acting as a base and carrier, is soothing to the scalp and promotes healing, is a lubricant and helps to groom and to manage unruly hair. The castor oil ingredient functions as a lubricant.

The hair dressing composition according to the present invention has been used successfully by both males and females, both black and white, with a variety of hair problems and conditions. These have ranged from short thin hair, brittle hair, unruly and unmanageable hair, and the like.

The composition according to the present invention is further illustrated by the following exemplary formulations:

Example 1

| First Ingredient: | Mixture of: | |
|---|---|---|
| Petroleum | 88.01% | 15.84 parts by weight |
| Rectified Tar Oil | 6.71% | 1.21 parts by weight |
| Sulfur | 2.43% | .44 parts by weight |
| Lanolin (Cosmetic) | 1.00% | .18 parts by weight |
| Captan (N-trichloromethylthio-4-cyclohexene-1,2 dicarboximide | 0.32% | .06 parts by weight |
| Inert | 1.53% | .27 parts by weight |
| | 100.00% | 18.00 parts by weight |
| or Glover's Sarcoptic Mange Medicine | | 18.00 parts |
| Second Ingredient: | | Mixture of: |
| Petrolatum | | 40 to 75% by weight |
| Mineral Oil | | 10 to 35% by weight |
| Mineral Wax | | 5 to 20% by weight |
| Isopropyl palmitate | | 5 to 20% by weight |
| Beeswax (synthetic) | | 5 to 20% by weight |
| Precipitated sulfur, U.S.P. | | 3 to 5% by weight |
| Rose Geranium Oil | | 0.5 to 3% by weight |
| Phenol, U.S.P. | | 0.05 to 0.15% by weight |
| Oxyquinoline | | 0.1 to 3% by weight |
| Pine Oil | | 0.1 to 3% by weight |
| | | To make 100% |
| or Cuticura Ointment | | 17.00 parts |
| Third Ingredient: Castor Oil | | 16.00 parts |
| Fourth Ingredient: Petroleum Jelly | | 336.00 parts |
| Total | | 387.00 |

Examples 2–9

| Example No. | 2 | 3 | 4 | 5 | 6 | 7 | 8 | 9 |
|---|---|---|---|---|---|---|---|---|
| First Ingredient Mixture | 18 | 19 | 20 | 18 | 18 | 17 | 16 | 19 |
| Second Ingredient Mixture (Cuticura) Ointment | 17 | 18 | 19 | 19 | 17 | 16 | 15 | 18 |
| Third Ingredient | | | | | | | | |

Examples 2–9-continued

| Example No. | 2 | 3 | 4 | 5 | 6 | 7 | 8 | 9 |
|---|---|---|---|---|---|---|---|---|
| (Castor Oil) | 16 | 15 | 18 | 17 | 16 | 14 | 14 | 18 |
| Fourth Ingredient (Petroleum Jelly) | 384 | 368 | 400 | 352 | 288 | 384 | 280 | 384 |
| Total parts by weight | 435 | 420 | 457 | 406 | 339 | 431 | 325 | 439 |

It is apparent that many modifications and variations of this invention as hereinbefore set forth may be made without departing from the spirit and scope thereof. The specific embodiments described are given by way of example only and the invention is limited only by the terms of the appended claims.

The embodiments of the invention in which an exclusive property or privilege is claimed are defined as follows:

1. An emollient hair grooming composition comprising a blended mixture of about 16 to 20 parts by weight of (A) a mixture consisting essentially of about 6.71% rectified tar oil, 2.43% sulfur, 1% lanolin, 1.53% inerts and 0.32% captan in 88.01% petroleum; about 15 to 19 parts by weight of (B) a mixture consisting essentially of about 10 to 35% by weight of mineral oil, about 5 to 20% each of mineral wax, isopropyl palmitate and beeswax, about 3 to 5% of sulfur, and about 0.1 to 3% each of oxyquinoline and pine oil in 40% to 75% of petroleum jelly containing about 0.1% phenol, to make 100%; and about 14 to 18 parts of (C) castor oil; all blended into about 280 to 400 parts by weight of (D) petroleum jelly.

2. The composition according to claim 1 further characterized in that said mixture includes a minor amount of an odorant.

3. The composition according to claim 2 further characterized in that said odorant is rose geranium oil.

4. The composition according to claim 3 further characterized in that said rose geranium oil is present in an amount between about 0.5 to 3%.

* * * * *